(12) United States Patent
Ceisel et al.

(10) Patent No.: US 7,517,148 B2
(45) Date of Patent: Apr. 14, 2009

(54) DENTAL DEVICE HAVING A SENSOR FILM HOLDER WITH TOOTH CLAMP

(76) Inventors: Robert J. Ceisel, 1450 Ammer Rd., Glenview, IL (US) 60025; Emily M. Ceisel, 1450 Ammer Rd., Glenview, IL (US) 60025

( * ) Notice: Subject to any disclaimer, the term of this patent is extended or adjusted under 35 U.S.C. 154(b) by 99 days.

(21) Appl. No.: 11/692,899

(22) Filed: Mar. 28, 2007

(65) Prior Publication Data

US 2008/0241786 A1 Oct. 2, 2008

(51) Int. Cl.
*A61B 6/14* (2006.01)
*A61C 5/12* (2006.01)

(52) U.S. Cl. .................. 378/191; 378/168; 378/169; 378/170; 433/139

(58) Field of Classification Search .................. 378/168, 378/169, 170, 191, 177; 433/139
See application file for complete search history.

(56) References Cited

U.S. PATENT DOCUMENTS

| | | | | |
|---|---|---|---|---|
| 1,520,753 A | * | 12/1924 | Ivory | 433/139 |
| 4,592,084 A | * | 5/1986 | McAuslan | 378/170 |
| 4,593,401 A | * | 6/1986 | Colbert | 378/168 |
| 4,661,063 A | * | 4/1987 | Levy | 433/139 |
| 6,609,911 B2 | * | 8/2003 | Garrison | 433/139 |
| 6,932,505 B2 | * | 8/2005 | Yao et al. | 378/170 |
| 2008/0090205 A1 | * | 4/2008 | Kilcher et al. | 433/139 |

* cited by examiner

*Primary Examiner*—Allen C. Ho
(74) *Attorney, Agent, or Firm*—Davis Michael Chin, Jr.; Davis Chin

(57) ABSTRACT

A dental device includes a housing unit for removably holding sensor film and a tooth clamp disposed on the housing unit. The tooth clamp consists of first and second resilient arcuate bridges. Each of the first and second bridge has a first and second end. The first end of the first bridge and the first end of the second bridge are interconnected to one jaw of a pair of oppositely disposed jaws. The second end of the first bridge and the second end of the second bridge are interconnected to the other jaw of the pair of oppositely disposed jaws. Each of the oppositely disposed jaws includes a gripping plate, an aperture and a tab for engaging a flexible sheet.

19 Claims, 4 Drawing Sheets

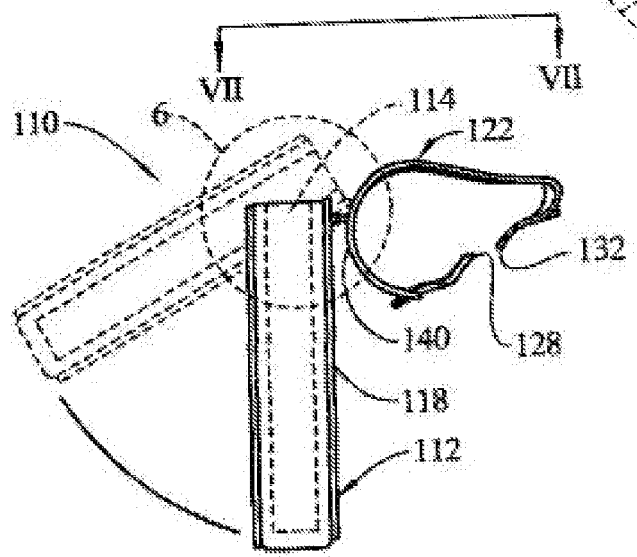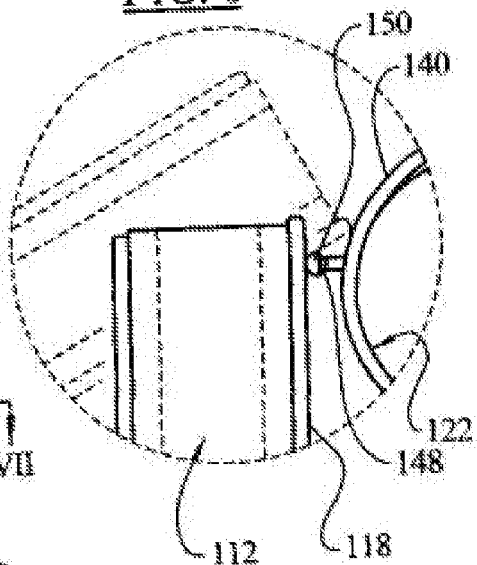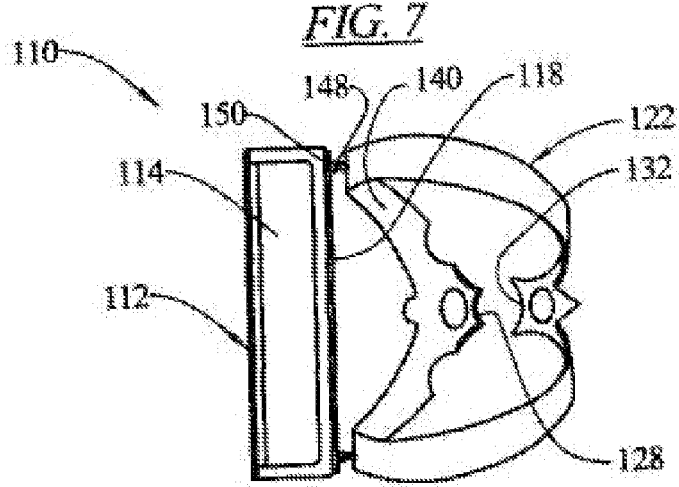

DENTAL DEVICE HAVING A SENSOR FILM HOLDER WITH TOOTH CLAMP

BACKGROUND OF THE INVENTION

1. Field of the Invention

This invention relates generally to dental devices, and more particularly, the present invention relates to an improved dental device formed of a sensor film holder with a tooth clamp, which allows, during treatment of a tooth, the simple and expedient placement of radiographic sensor film or digital sensor, within the oral cavity of a patient without having to remove or adjust the already placed rubber dam.

2. Description of the Prior Art

Over the past years, advancements in dentistry have improved greatly, especially since the discovery and use of dental radiography. The applications of dental radiography have enhanced the efficiency and effectiveness of many dental operations, such as in root canal treatment (RCT).

Generally, RCT's and other dental procedures are performed with a flexible sheet, such as a rubber dam, in a surrounding relation to the tooth or teeth undergoing treatment. The rubber dam isolates the tooth from the rest of the interior of the patient's oral cavity and prevents ingestion of medicine or other substances by the patient. Another function of the rubber dam is to create a sterile environment within the oral cavity by preventing bacteria and other contaminants from entering the patient's tooth during the dental procedure.

Procedurally, a hole is punched into the rubber dam. The hole should be of a size smaller than the outer profile of the operative tooth. Typically, the rubber dam is secured in a proper position around the tooth by way of a dental clamp. The dental clamp includes an arcuate bridge which interconnects a pair of laterally opposed jaws. The opposed jaws are designed to grip the tooth immediately above the gum line. Once the rubber dam and dental clamp have been properly mounted on the tooth by use of forceps, the hole of the rubber dam shrinks snugly around the circumferential neck of the tooth. Then, a dam frame, such as a Young's frame, is secured onto the outer periphery of the rubber dam, and outside of the patient's mouth, in order to keep the rubber dam taut.

During dental procedures which require the use of a rubber dam, it may be necessary for the dentist to remove or adjust the rubber dam in order to monitor the progress of the procedure. For example, while monitoring the progress of a RCT it is standard practice to take a radiograph before the completion of the procedure. Similarly, in the course of particular endodontic procedures it is necessary to take multiple radiographs during wire measurements. Thus, it is necessary for the dentist to position the sensor film at a location between the oral cavity and the underside of the rubber dam. This requires the dentist to either remove the rubber dam completely or at least, with the use of certain sensor film holders, remove the frame of the rubber dam, which is not always easy or comfortable for the patient. As can be guessed, the possibility of contaminants entering the patient's mouth or tooth is an issue because of the movement of the rubber dam causing leakage and contamination of the field.

Usually during an RCT, the dentist will use hemostatic forceps to then place the sensor film within the patient's mouth and the patient will hold the forceps in place with his hand while the radiograph is being taken. In order to eliminate image distortions and improper focus of the radiograph, it is essential for the sensor film to be placed properly within the patient's mouth and for the forceps to be held steady by the patient. More often than not, a patient will inadvertently move during the taking of the radiograph causing the need to retake the radiograph and exposing the patient to additional radiation. Likewise, in the course of endodontic procedures, which require the taking of multiple radiographs during wire measurements, it is essential to take only the minimal number of radiographs so the patient is only exposed to the least amount of radiation.

Another concern for the patient besides additional exposure to radiation is the sterility of the sensor film. While current technology employs chemicals to sterilize items that are used multiple times, there is still a possibility that the sensor film holder may contain viruses, bacteria, hepatitis B, pirons and/or some other pathogens which are not killed or inactivated. In efforts to mitigate these germs from contact with the patient, the sensor film holders can be wiped down or have a plastic sheath placed over them, but over time this system can easily be breached. For example, in many instances, after removal of the plastic sheath the sensor film holder is merely wiped off when the procedure is completed and then a new plastic sheath, similar to cellophane wrap, is placed over the sensor film holder and a new sensor film, in preparation for use in the next procedure.

In view of these problems, attempts have been made heretofore in the prior art to develop new implementations so as to reduce contaminants from entering the patient's mouth during dental procedures, such as the ones discussed above, and to eliminate unnecessary exposure of radiation to the patient. For example, one such improvement includes a sensor holder which accommodates different sizes of sensors so as to prevent the sensor covers from being stripped when placed in the sensor holder. Another example is a bite block sensor holder which attempts to steady the sensor film in a stationary position.

Although these improvements may have performed so as to lessen the chance of contaminants from coming into contact with patient's skin or fluid and to keep the sensor film steady, these improvements did not eliminate the practice of adjusting the rubber dam in order to place the sensor film between the oral cavity and the underside of the rubber dam.

Therefore, it should come as no surprise that sensor film holders have been developed and constructed heretofore in the prior art so as to minimize the chance of contaminants, which may be on the sensor film, from coming into contact with the patient's skin and to maintain the sensor holder in a steady stationary position. In spite of these efforts in the prior art, it would be still desirable to provide an improved dental device formed of a sensor film holder with a tooth clamp which would entirely eliminate contact of the sensor film with the patient's skin or fluid and to make certain that the sensor holder is maintained in a steady position.

A prior art search directed to the subject matter of this application in the U.S. Patent and Trademark Office revealed the following Letters Patent:

| |
|---|
| 1,398,247 |
| 1,434,894 |
| 1,585,264 |
| 1,785,624 |
| 1,899,877 |
| 2,010,646 |
| 2,240,336 |
| 2,786,947 |
| 4,639,221 |
| 5,784,433 |
| 6,540,399 |
| 6,609,911 |

U.S. Pat. No. 6,609,911 to Garrison issued on Aug. 26, 2003, discloses a dental clamp which includes a resilient arcuate bridge connecting a pair of opposing jaws. In particular, each jaw includes a plate with an aperture therethrough, a dam tab and resilient fingers. Additionally, the '911 patent also discloses alternative embodiments for use on different types of teeth (e.g., molar, bicuspid).

U.S. Pat. No. 1,785,624 to Haller, issued on Dec. 16, 1930, teaches a tooth clamp which was designed to protect against gum injury during use of the clamp. This metal tooth clamp includes a resilient bow connected to a pair of opposing arms, which are stepped towards the end of the roots of the tooth and extend on the inner side and outer side of the gum.

Further, U.S. Pat. No. 1,585,264 to Rosenthal issued on May 18, 1926 discloses a holder for holding film during the taking of intraoral radiographs of teeth. The holder may be made of radiolucent material and may be provided with an aperture in its front wall to permit the free passage of the rays. The holder is designed to contain two film packets, in side-by-side relation. During a dental procedure, the film packets may be removed easily through the upper opening in the holder. The '264 patent discloses that the holder may be held stationary in the mouth during successive exposures by mechanical means.

The remaining patents, listed above but not specifically discussed, are deemed to be only of general interest and show the state of the art in devices used in dental procedures.

None of the prior art discussed above discloses a dental device formed of a sensor film holder with an attachable tooth clamp like that of the present invention which eliminates the need, during a dental procedure, for the user to remove or adjust the already placed rubber dam so as to limit the possible transfer of fatal or contagious diseases, thereby realizing an important goal of dentistry.

SUMMARY OF THE INVENTION

Accordingly, it is a general object of the present invention to provide an improved dental device formed of a sensor film holder with a tooth clamp which eliminates contact of the sensor film holder with patient's fluid or skin and overcomes the disadvantages of the prior art.

It is an object of the present invention to provide an improved dental device which includes a sensor film holder with an attachable tooth clamp.

It is another object of the present invention to provide an improved dental device which allows for more precise alignment and reduction in angulation difficulties when taking radiographs during dental procedures, thus reducing patient exposure to excessive radiation due to the retaking of radiographs because of distorted or unfocused images from initially missed alignment. The final result of the RCT will be enhanced due to the increased accuracy of the radiograph, thus improving predictability of treatment for the patient.

It is another object of the present invention to provide an improved dental device which is cost effective to manufacture and which is relatively easy and non-problematic to use in operation.

In a preferred embodiment of the present invention, there is provided a dental device which allows for the simple and expedient placement of radiographic sensor film within the oral cavity of a patient without having to remove or adjust the already placed rubber dam. The dental device includes a housing unit for removably holding sensor film, which is attachable to first and second resilient arcuate bridges. Each of the first and second bridges has a first and second end. The first end of the first bridge and the first end of the second bridge are interconnected to corresponding opposite sides of one jaw of a pair of oppositely disposed jaws. The second end of the first bridge and the second end of the second bridge are interconnected to corresponding opposite sides of the other jaw of the pair of oppositely disposed jaws. Each of the oppositely disposed jaws includes a gripping plate, an aperture and a tab for engaging a flexible sheet.

BRIEF DESCRIPTION OF THE DRAWINGS

These and other objects and advantages of the present invention will become more fully apparent from the following detailed description when read in conjunction with the accompanying drawings with like reference numerals indicating corresponding parts throughout, wherein:

FIG. 5 is a side view of a second embodiment of an improved dental device 110 which includes a sensor film holder having a pivotally attachable tooth clamp;

FIG. 6 is an enlarged view of the encircled portion 6 of the dental device in FIG. 5; and FIG. 7 is a top view of the dental device, taken along the lines VII-VII of FIG. 5.

DESCRIPTION OF THE PREFERRED EMBODIMENTS

Figure 1:
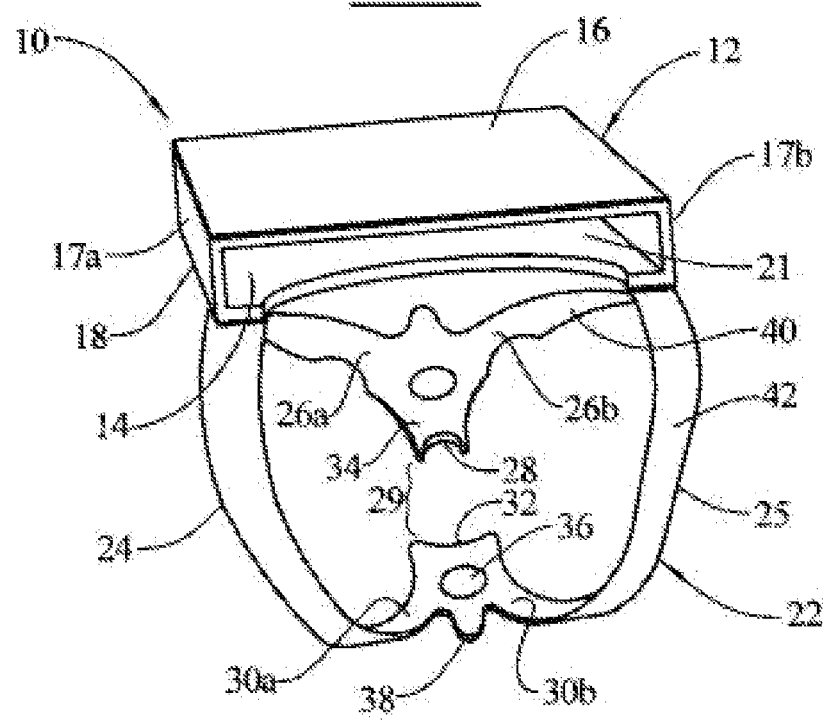
FIG. 1 is a perspective view of an improved dental device, constructed in accordance with the principles of the present invention.

It is to be distinctly understood at the outset that the present invention shown in the drawings and described in detail in conjunction with the preferred embodiments is not intended to serve as a limitation upon the scope or teachings thereof, but is to be considered merely as an exemplification of the principles of the present invention.

Figure 2:
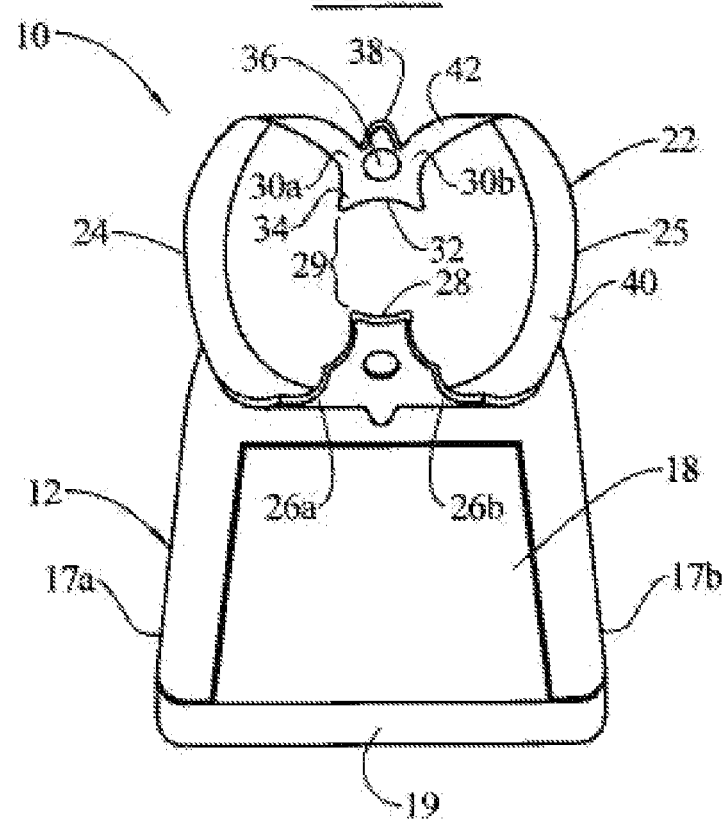
FIG. 2 is a bottom plan view of the improved dental device of FIG. 1.
Figure 3:
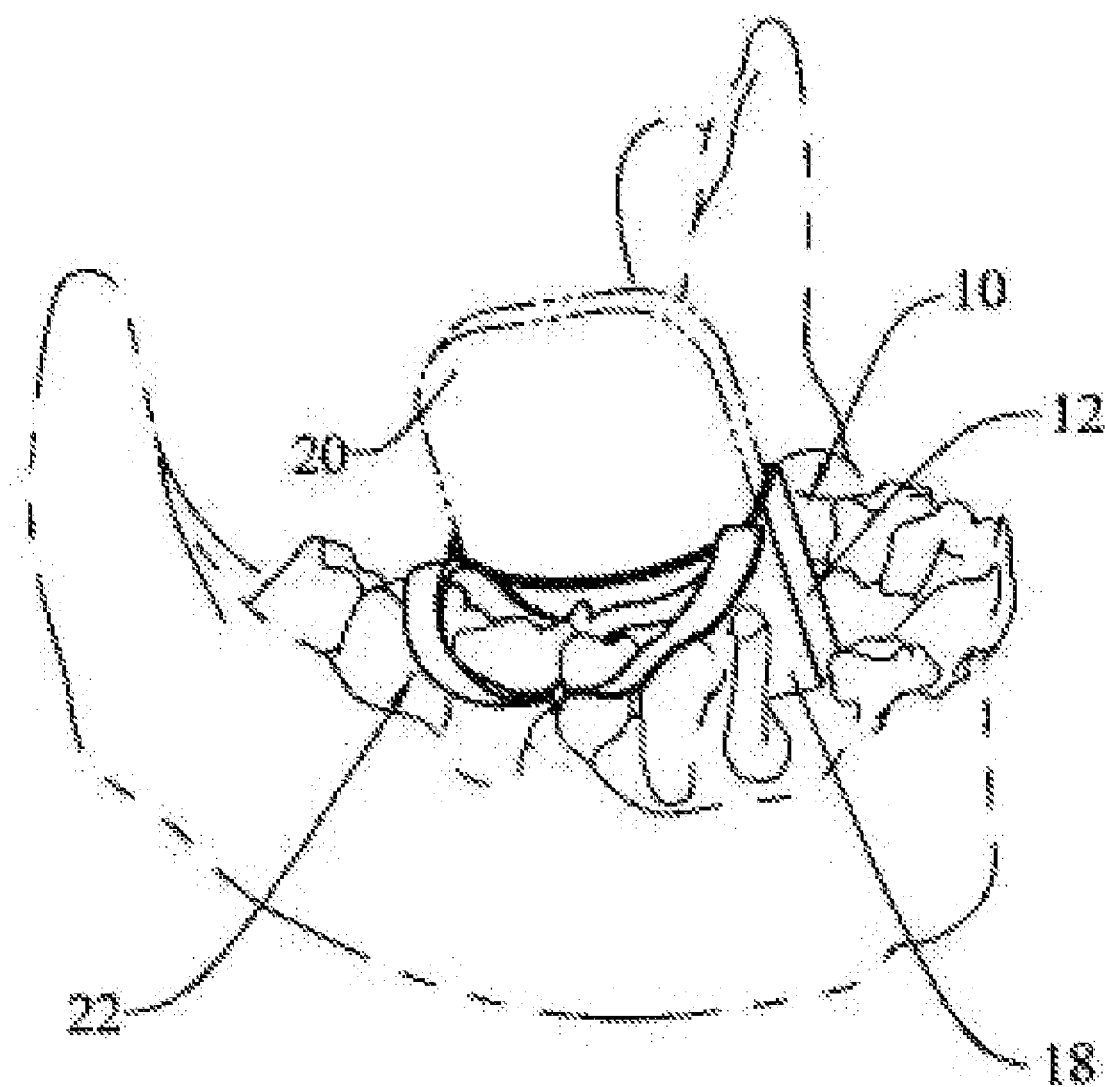
FIG. 3 is a perspective view of the improved dental device of FIG. 1 depicting the sensor film holder mounted onto a tooth, with the rubber dam being removed for clarity.
Figure 4:
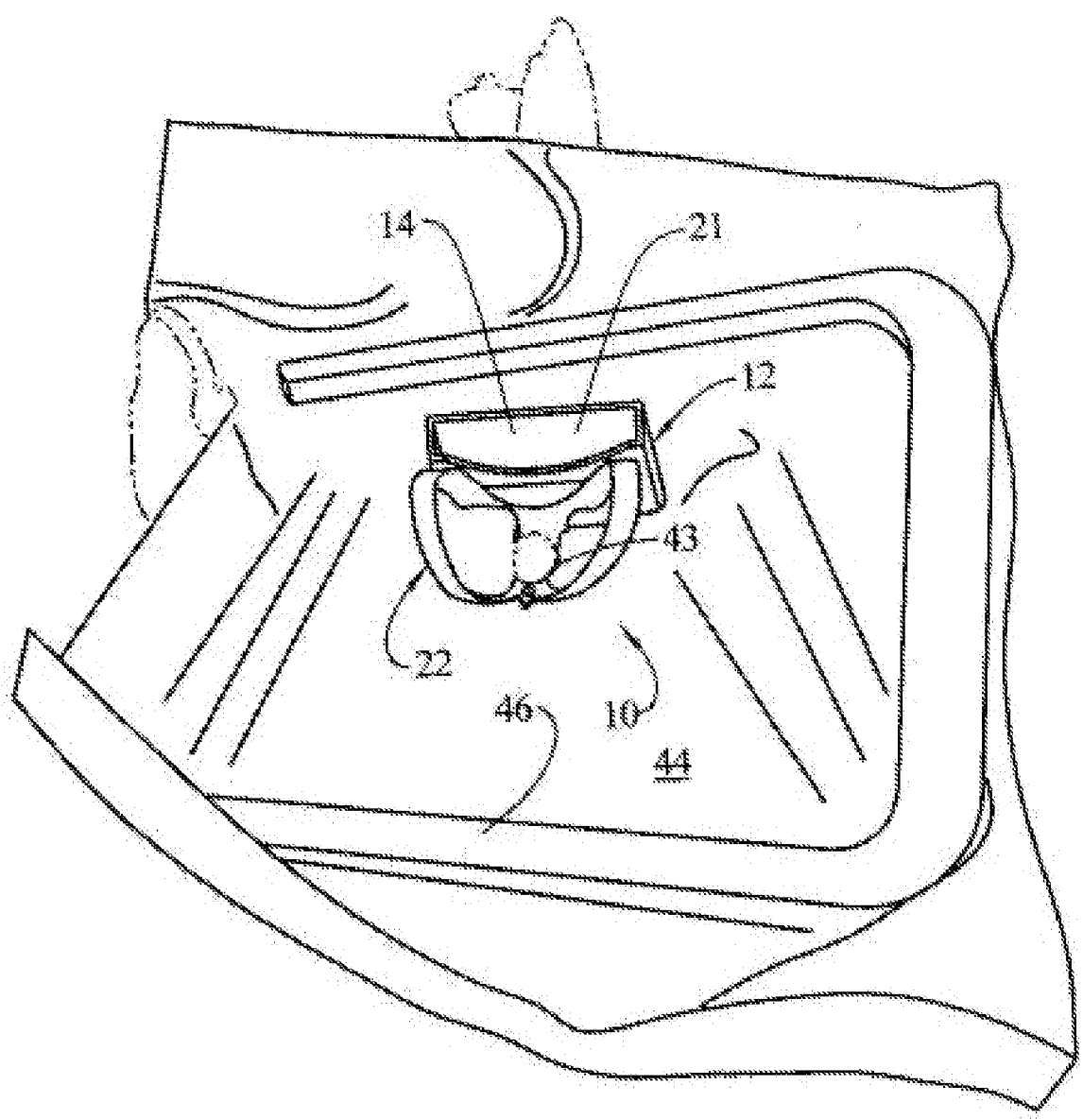
FIG. 4 is a perspective view of the improved dental device of FIG. 1 depicting the sensor film holder mounted onto a tooth with the use of a rubber dam.

Referring now in detail to the drawings, wherein like reference characters designate like or corresponding parts throughout the several views, there is illustrated in FIGS. 1 through 4 an improved dental device 10 constructed in accordance with the principles of the present invention. In particular, FIG. 1 is a perspective view of the dental device 10. FIG. 2 is a bottom plan view of the dental device 10. FIG. 3 is a perspective view of the dental device 10 mounted onto a tooth with the rubber dam removed for the sake of clarity in illustration. FIG. 4 is a perspective view of the dental device 10 being mounted onto a tooth with the use of a rubber dam.

The dental device 10 includes a sensor film holder for removably holding a sensor film or a digital sensor. The use of the digital sensor allows for the recording of an x-ray image and then the image is converted to a digital radiograph for viewing on a computer screen. The sensor film holder is a substantially rectangular-shaped housing unit 12, forming a complete enclosure except for an elongated top opening 14. The housing unit 12 may be made of a radiolucent material, such as the types of metals or plastics used in the medical industry. The housing unit 12 includes a front wall 16, side walls 17a, 17b, a back wall 18 and a bottom wall 19 all interconnected together so as to form a cavity 21. The housing unit 12 is suitably dimensioned to removably accommodate a commercially available, standard sized radiographic film or digital sensor 20 disposed within the cavity 21. The housing unit may also be suitably designed and contoured to removably accommodate pedodontic and/or adult sized radiographic films or digital sensors. Furthermore, a screen may be placed in front of the sensor film to intensify the x-ray, which could lower radiation dose and improve sensor film reception.

Front wall 16 of the housing unit 12 may optionally include a reflective or mechanical aiming device (not shown) to facilitate x-ray beam alignment during the taking of a radiograph.

The dental device 10 also includes a tooth clamp portion 22, which is formed integrally with or fixedly mounted to the sensor film holder 12. Tooth clamp portion 22 includes a pair of resilient arcuate bridges 24, 25 which are identical and are positioned diametrically opposed to one another. The first ends 26a, 26b of each of the arcuate bridges 24, 25 are joined to corresponding sides of a first opposed jaw 28 defining a portion of a gripping device. Similarly, the second ends 30a, 30b of each of the arcuate bridges 24, 25 are joined to corresponding opposite sides of a second opposed jaw 32 defining also a portion of the gripping device.

The first and second opposed jaws 28, 32 define a space 29 therebetween for gripping the tooth undergoing treatment above the gum line. Each opposed jaw 28, 32 comprises a plate 34 with an aperture 36 therethrough and a dam tab 38. Opposed jaws 28, 32 may be designed to accommodate different types of teeth, i.e., molars, bicuspids, and the like. Tooth clamp portion 22 also includes a first side 40 and a second side 42. The tooth clamp 22 is applied by spreading the opposed jaws 28, 32 with a special forceps (not shown), positioning the space 29 between the jaws around the tooth, and then carefully releasing the jaws once the tooth clamp has been properly positioned.

Back wall 18 of housing unit 12 is fixedly mounted onto the first side 40 of tooth clamp portion 22 in a fashion so that elongated top opening 14 of the housing unit 12 is facing a substantially upward orientation and opposed jaws 28, 32 of the tooth clamp portion 22 are facing a substantially downward orientation. Alternatively, an additional housing unit, which is substantially identical to housing unit 12, may be also fixedly mounted onto the second side 42 of tooth clamp portion 22 so as to accommodate a second sensor film or digital sensor 20 to provide for computerized stereo viewing.

In use, the dental device 10 of the present invention is ultimately clamped onto the patient's tooth with the tooth clamp portion 22. Initially, a hole 43, of a size smaller than the outer profile of the operative tooth, is punched into the rubber dam 44 (FIG. 4). The hole 43 is then stretched over the opposed jaws 28, 32 and is held secured by use of the dam tabs 38. Further, the rubber dam 44 and the sensor film holder 10 are placed in position in the patient's mouth. Once the dam and holder are placed in proper position, a pair of special forceps (not shown) is used to fix the tooth clamp portion 22 onto the operative tooth. Lastly, a dam frame 46 is positioned around the outer periphery of the rubber dam 44 to produce tension in the dam 44.

Now that the dental device 10 and the rubber dam 44 are securely attached to the operative tooth, the housing unit 12 thereof is positioned on the isolation side of the rubber dam 44, i.e., the rubber dam 44 is located between the housing unit 12 and the patient's oral cavity. Since the housing unit 12 is not in contact with the patient's skin and is located in an easily accessible position, the dentist or assistant may freely place and replace sensor film in the housing unit 12 allowing the dentist or assistant to take multiple radiographs during the procedure without having to remove or adjust the rubber dam 44.

Given that the housing unit 12 of the dental device 10 is located on the isolation side of the rubber dam 44, the concern of contaminants entering the patient's mouth because of rubber dam movement during a dental procedure has been eliminated. Moreover, since the housing unit 12 of the dental device 10 is securely and stably attached to the tooth, inaccuracy in x-ray alignment and excessive radiation exposure to the patient is greatly reduced.

In FIG. 5, there is shown an alternative embodiment of a dental device 110 which is substantially identical in its construction, interconnections of elements and mode of operation of the dental device 10 depicted in FIGS. 1-4, except for the added feature discussed below. In this alternative embodiment, back wall 118 of housing unit 112 may be pivotally and/or removably attached onto the first side 140 of tooth clamp portion 122 in a fashion so that elongated top opening 114 of the housing unit 112 is facing a substantially upward orientation and opposed jaws 128, 132 of the tooth clamp portion 122 are facing a substantially downward orientation.

The pivotability of the housing unit 112 may be designed with a ball portion 148 located on the tooth clamp portion 122 and a socket portion 150 located on the back wall 118 of housing unit 112, as shown in FIGS. 5-7. In particular, FIG. 5 shows the housing unit 112, in phantom, wherein the ball portion 148 has been rotated with respect to the socket portion 150 to its fully extended pivotal position. Alternatively, the ball portion 148 may be located on the back wall 118 of housing unit 112 and the socket portion 150 may be located on the tooth clamp portion 122. This feature of a pivotal housing unit 112 allows for an even more precise technique for better alignment of the x-ray machine with the sensor film.

From the foregoing detailed description, it can thus be seen that the present invention provides an improved dental device which includes a sensor film holder and a tooth clamp portion fixedly mounted to the sensor film holder. As a result, the sensor film holder of the present invention is relatively easy to use, eliminates the need for removal and/or adjustment of the rubber dam during dental procedures which leads to steady, better alignment of the sensor film with the x-ray machine, decreases additional exposure of radiation to the patient and maintains a sterile environment in the patient's oral cavity. Thus, the present invention achieves an important goal in dentistry of limiting the possible transfer of fatal or contagious diseases, such as hepatitis B, pirons and other pathogens.

While there has been illustrated and described what is at present considered to be a preferred embodiment of the present invention, it will be understood by those skilled in the art that various changes and modifications may be made, and equivalents may be substituted for elements thereof without departing from the true scope of the invention. In addition, many modifications may be made to adapt a particular situation or material to the teachings of the invention without departing from the central scope thereof. Therefore, it is intended that this invention not be limited to the particular embodiment disclosed as the best mode contemplated for carrying out the invention, but that the invention will include all embodiments falling within the scope of the appended claims.

The invention claimed is:

1. A dental device for use during a dental procedure so as to eliminate the need for removal or adjustment of an already placed flexible sheet, comprising in combination:
   a housing unit for removably holding sensor film;
   a tooth clamp formed of a first resilient arcuate bridge and a second resilient arcuate bridge;

said first resilient arcuate bridge having a first end and a second end;

said second resilient arcuate bridge having a first end and a second end;

oppositely disposed first and second jaws, each of said oppositely disposed first and second jaws having a gripping plate, said gripping plate including an aperture and a tab engagable with a flexible sheet;

said first end of said first resilient arcuate bridge and said first end of said second resilient arcuate bridge being connected to corresponding opposite sides of one of said oppositely disposed first and second jaws;

said second end of said first resilient arcuate bridge and said second end of said second resilient arcuate bridge being connected to corresponding opposite sides of the other one of said oppositely disposed first and second jaws; and said housing unit being disposed on said tooth clamp.

2. A dental device as claimed in claim 1, wherein said housing unit is pivotally attached to said tooth clamp.

3. A dental device as claimed in claim 2, further comprising ball and socket means for pivotally attaching said tooth clamp to said housing unit.

4. A dental device as claimed in claim 1, wherein said housing unit is removably attached to said tooth clamp.

5. A dental device as claimed in claim 1, wherein said housing unit is of a substantially rectangular shape.

6. A dental device as claimed in claim 1, wherein the housing unit is made of a radiolucent material.

7. A dental device for use during a dental procedure so as to eliminate the need for removal or adjustment of an already placed flexible sheet comprising in combination:

means for removably holding sensor film;

a tooth clamp formed of a first resilient arcuate bridge and a second resilient arcuate bridge;

said first resilient arcuate bridge having a first end and a second end;

aid second resilient arcuate bridge having a first end and a second end;

a pair of oppositely disposed gripping means for gripping a tooth;

said first end of said first resilient arcuate bridge and said first end of said second resilient arcuate bridge being connected to corresponding opposite sides of one of said pair of oppositely disposed gripping means;

said second end of said first resilient arcuate bridge and said second end of said second resilient arcuate bridge being connected to corresponding opposite sides of the other one of said pair of oppositely disposed gripping means; and said means for removably holding sensor film being disposed on said tooth clamp.

8. A dental device as claimed in claim 7, wherein said means for removably holding sensor film is pivotally attached to said tooth clamp.

9. A dental device as claimed in claim 8, further comprising ball and socket means for pivotally attaching said tooth clamp to said means for removably holding sensor film.

10. A dental device as claimed in claim 7, wherein said means for removably holding sensor film is removably attached to said tooth clamp.

11. A dental device as claimed in claim 7, wherein said means for removably holding sensor film is of a substantially rectangular shape.

12. A dental device as claimed in claim 7, wherein each of said pair of oppositely disposed gripping means includes a jaw.

13. A dental device as claimed in claim 7, wherein each of said pair of oppositely disposed gripping means includes a tab for engaging a flexible sheet.

14. A dental device for use during a dental procedure comprising:

a pair of oppositely disposed gripping means for gripping a tooth;

bridge means for connecting said pair of oppositely disposed gripping means;

means for removably holding sensor film;

said means for removably holding sensor film being interconnected to said bridge means; and said means for removably holding sensor film being pivotally attached to said bridge means for connecting said pair of oppositely disposed gripping means.

15. A dental device as claimed in claim 14, further comprising a ball and socket means for pivotally attaching said bridge means to said means for removably holding sensor film.

16. A dental device as claimed in claim 14, wherein said means for removably holding sensor film is removably attached to said bridge means for connecting said pair of oppositely disposed gripping means.

17. A dental device as claimed in claim 14, wherein said means for removably holding sensor film is of a substantially rectangular shape.

18. A dental device for use during a dental procedure comprising:

a pair of oppositely disposed gripping means for gripping a tooth;

each of said pair of oppositely disposed gripping means including a jaw;

bridge means for connecting said pair of oppositely disposed gripping means;

means for removably holding sensor film; and said means for removably holding sensor film being interconnected to said bridge means.

19. A dental device for use during a dental procedure comprising:

a pair of oppositely disposed gripping means for gripping a tooth;

each of said pair of oppositely disposed gripping means including a tab for engaging a flexible sheet;

bridge means for connecting said pair of oppositely disposed gripping means;

means for removably holding sensor film; and said means for removably holding sensor film being interconnected to said bridge means.

* * * * *